(12) United States Patent
Styrc

(10) Patent No.: US 9,980,814 B2
(45) Date of Patent: May 29, 2018

(54) KIT FOR PROCESSING A BLOOD CIRCULATION PIPE

(75) Inventor: Mikolaj Styrc, Kopstal (LU)

(73) Assignee: CORMOVE, Bornel (FR)

( * ) Notice: Subject to any disclaimer, the term of this patent is extended or adjusted under 35 U.S.C. 154(b) by 358 days.

(21) Appl. No.: 12/602,310

(22) PCT Filed: May 30, 2008

(86) PCT No.: PCT/FR2008/050957
§ 371 (c)(1),
(2), (4) Date: May 5, 2010

(87) PCT Pub. No.: WO2008/152318
PCT Pub. Date: Dec. 18, 2008

(65) Prior Publication Data
US 2010/0256754 A1  Oct. 7, 2010

(30) Foreign Application Priority Data
May 30, 2007 (FR) ...................................... 07 55355

(51) Int. Cl.
*A61F 2/24* (2006.01)

(52) U.S. Cl.
CPC .......... *A61F 2/2412* (2013.01); *A61F 2/2475* (2013.01); *A61F 2/2409* (2013.01); *A61F 2/2436* (2013.01); *A61F 2250/0003* (2013.01); *A61F 2250/006* (2013.01); *A61F 2250/0015* (2013.01); *A61F 2250/0018* (2013.01)

(58) Field of Classification Search
CPC .... A61F 2/2409; A61F 2/2412; A61F 2/2418; A61F 2/2475

USPC .. 623/1.24, 1.27, 2.1, 2.12, 2.14, 2.17–2.18, 623/2.38
See application file for complete search history.

(56) References Cited

U.S. PATENT DOCUMENTS

| | | | |
|---|---|---|---|
| 6,312,465 B1 * | 11/2001 | Griffin et al. | 623/2.38 |
| 2006/0178731 A1 | 8/2006 | Tower | |
| 2006/0287717 A1 * | 12/2006 | Rowe et al. | 623/2.11 |
| 2007/0255394 A1 * | 11/2007 | Ryan | 623/1.24 |

FOREIGN PATENT DOCUMENTS

| | | | | |
|---|---|---|---|---|
| WO | WO 2006/054107 | * | 5/2006 | A61F 2/24 |
| WO | WO 2006/128185 | | 11/2006 | |
| WO | WO 2007/149933 A2 | * | 12/2007 | A61F 2/24 |

* cited by examiner

*Primary Examiner* — Leslie Lopez
(74) *Attorney, Agent, or Firm* — Berenato & White, LLC

(57) ABSTRACT

The kit (10) of the invention includes a valve bearing (16) that can be radially deformed. The bearing (16) includes an outer peripheral wall (22) defining a central passage (40) having an axis (X-X'). The bearing (16) further includes an inner peripheral wall (24) defining an inner lumen (44) having a radial dimension lower than that of the central passage (40). The kit (10) includes a prosthetic valve (18) to be placed on the inner peripheral wall (24). The inner peripheral wall (24) extends in the central passage axially relative to the outer wall (22). The valve bearing (16) includes a means (26) for maintaining the inner peripheral wall (24) radially remote from the outer peripheral wall (22). The inner peripheral wall (24) and the maintaining means (26) define an inner blood circulation region (56) containing the lumen (44) which is tightly isolated from an outer region (58).

19 Claims, 4 Drawing Sheets

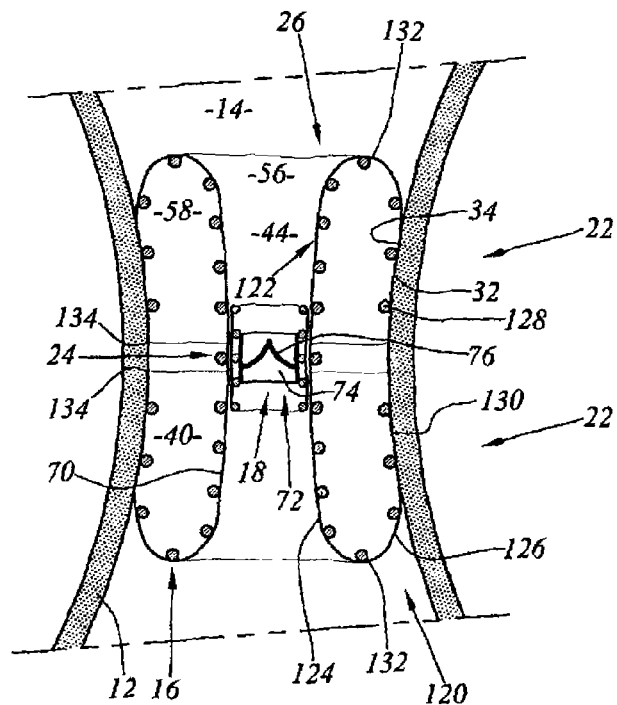
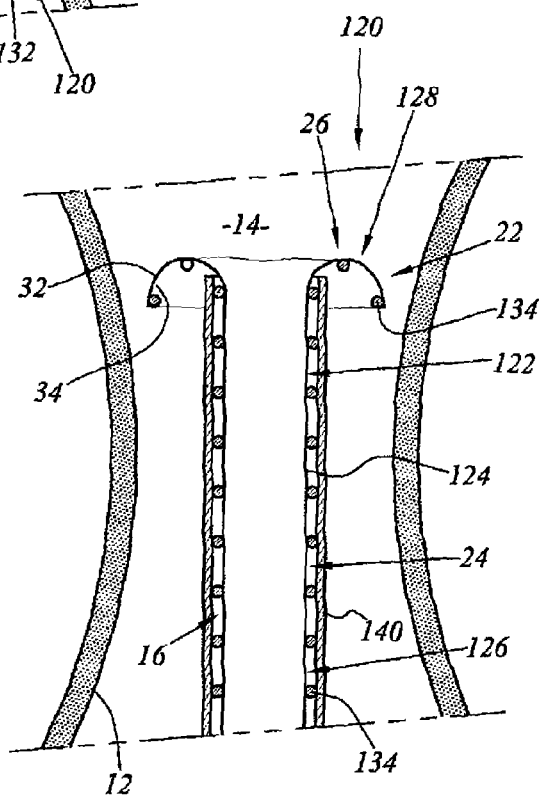

KIT FOR PROCESSING A BLOOD CIRCULATION PIPE

The present invention relates to a kit for treating a blood circulation vessel, of the type comprising:
- a valve support which can be deformed radially between a contracted state and a dilated state, the valve support comprising:
    - at least one external peripheral wall which is intended to press against a wall of the blood circulation vessel, the external peripheral wall delimiting a central passage having a centre axis;
    - an internal peripheral wall which is fixedly joined to the external peripheral wall and which delimits an internal aperture having a radial dimension which is smaller than that of the central passage; and
    - means for retaining the internal peripheral wall at least partially with radial spacing from the or each external peripheral wall; and
- a prosthetic valve which comprises a shutter which can be radially deformed and which is intended to be positioned on the internal peripheral wall in the aperture in order to selectively block the aperture;

the retention means and the internal peripheral wall delimiting in a fluid-tight manner an inner blood circulation region which opens at the proximal and distal ends of the valve support and which contains the aperture, and an external annular region in order to force the blood which flows in the vessel to pass into the inner region through the aperture.

Such a kit is intended to be implanted in place of a cardiac valve, such as, for example, the pulmonary valve located at the outflow of the right ventricle. This valve ensures one-way circulation of the blood flow which prevents reflux of blood following the ventricular contraction.

Diseases affect the valves. In particular, they may suffer from poor opening, thus reducing the blood flow, or be only partially fluid-tight, thus allowing reflux or regurgitation towards the ventricle which has discharged the blood flow.

It is known to treat this type of disease in a surgical manner, by replacing the affected valve. To this end, it is known to implant in the ventricular outflow tract, in place of a defective valve, a prosthetic valve which is formed by an annular metal armature and a flexible shutter which is produced from a tissue of animal origin. The shutter is permanently fixed to the armature.

Such valves have the advantage of being able to be implanted via the percutaneous route, which limits the risks involved with major surgery, in particular for patients who are elderly or weakened by other diseases. The tissue of animal origin which constitutes the shutter is generally obtained from valves of bovine jugular veins which are removed from animals. Such valves are generally available up to diameters of approximately 22 mm.

Such valves can therefore be used only for patients who have a ventricular outflow tract having a diameter of less than approximately 25 mm. However, approximately 75% of patients have a ventricular outflow tract having a diameter greater than 25 mm.

In order to solve this problem, a kit of the above-mentioned type is known from the article "Percutaneous Pulmonary Valve Replacement in a Large Right Ventricular Outflow Tract", Journal of the American College of Cardiology, Volume 43, 2004. This kit comprises a valve support which has a tubular armature which has two end collars having large diameters (greater than 25 mm) which are intended to move into abutment with the walls of the ventricular outflow tract and a central portion having a diameter of less than 22 mm, which is intended to internally receive the flexible tissue shutter.

Such a kit is not entirely satisfactory. In order to provide adequate fixing of the valve support in the vessel, the collars must have a significant length which increases the length of the valve support and makes its positioning difficult and imprecise.

An object of the invention is therefore to obtain a treatment kit which has a valve support which is capable of being readily implanted in a precise manner in a vessel having a large diameter, whilst being capable of receiving an animal valve having a small diameter.

To this end, the invention relates to a kit of the above-mentioned type, characterised in that the internal peripheral wall extends in the central passage, axially in register with the or each external peripheral wall.

The kit according to the invention may comprise one or more of the following features, taken in isolation or according to any technically possible combination:
- the external peripheral wall comprises a tubular armature, the internal peripheral wall comprising a tube which is arranged completely inside the central passage;
- the retention means comprise a distal peripheral skirt and a proximal peripheral skirt which extend in the space located between the internal peripheral wall and the external peripheral wall;
- the armature is formed by a rigid open-work trellis, the tube being a flexible tube;
- the armature is formed by an external tubular open-work trellis, the tube being formed by an internal open-work trellis which has a diameter smaller than that of the external trellis;
- the valve support comprises an inflatable sleeve which is fixed to the external peripheral wall, the internal peripheral wall being fixed to or delimited by the inflatable sleeve;
- the valve support comprises a single tubular armature which comprises a central tubular portion which forms the internal peripheral wall and two end portions which are turned over outside and around the central portion, each end portion forming an external peripheral wall and means for retaining the internal peripheral wall with spacing from the external peripheral wall;
- the two end portions can be deformed spontaneously between a configuration for introducing the valve support into the vessel, in which they extend coaxially in continuation of the central portion, and an operating configuration, in which they are turned over around the central portion;
- the central aperture has a transverse dimension of less than 35 mm;
- the prosthetic valve is a valve which can be moved relative to the internal peripheral wall, the movable valve comprising a supporting armature, to which the shutter is fixed; and
- the prosthetic valve is permanently fixed to the internal peripheral wall.

The invention will be better understood from a reading of the following description, given purely by way of example, and with reference to the appended drawings, in which:

FIG. 5 is a view similar to FIG. 1 of a fourth treatment kit according to the invention;

FIG. 6 is a view similar to FIG. 2 during the implantation of the valve support of the kit of FIG. 5.

Figure 1:
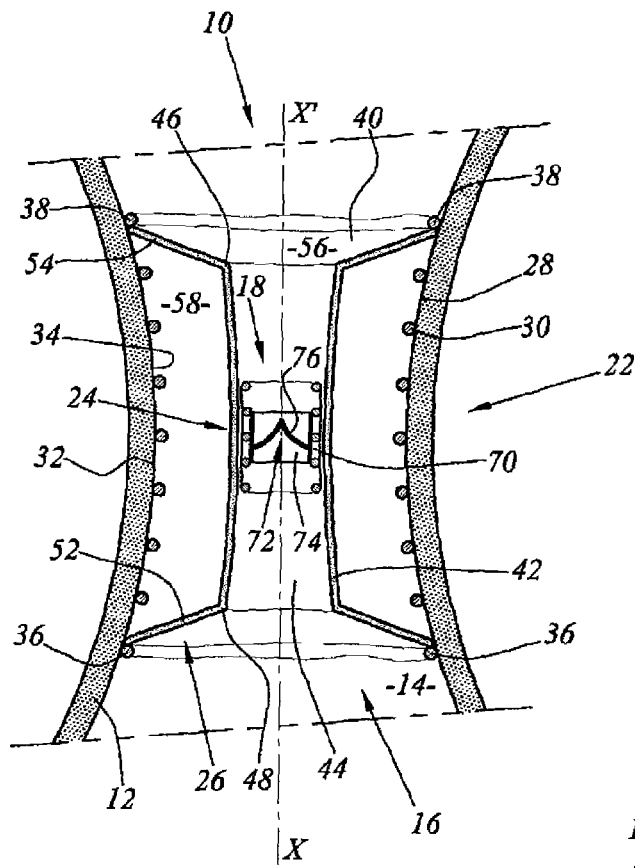
FIG. 1 is a section along a centre plane of a first kit according to the invention, implanted in a blood circulation vessel.
Figure 2:
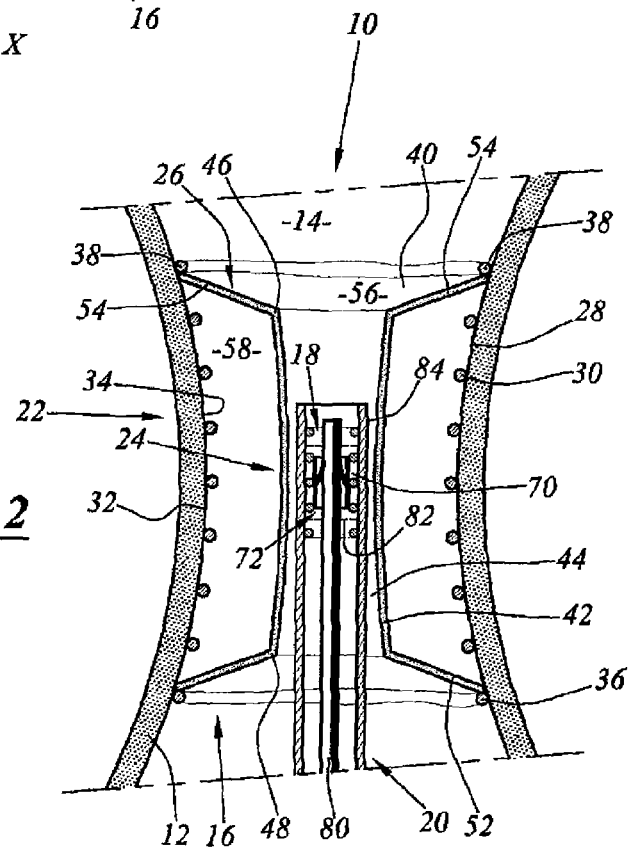
FIG. 2 is a view similar to FIG. 1, during the implantation of the prosthetic valve of the kit of FIG. 1.

A first kit 10 according to the invention is illustrated in FIGS. 1 and 2.

This kit is intended to be implanted, for example, against an internal wall 12 of a ventricular outflow tract which delimits a blood circulation vessel 14, in place of a natural pulmonary valve.

The kit 10 comprises a valve support 16 which is intended to be pressed against the internal wall 12 and a removable prosthetic valve 18 which is carried by the valve support 16 in order to provide one-way circulation of the blood flow in the vessel 14.

The kit 10 further comprises a release device of the support 16 (not illustrated) and a tool 20 for releasing the valve 18, which can be seen in FIG. 2.

As illustrated in FIG. 1, the valve support 16 comprises an external peripheral wall 22 for rigid abutment against the inner surface 12, an internal peripheral wall 24 which is arranged in the wall 22 in order to carry the valve 18 and, for connection between the internal wall 24 and the external wall 26, means 26 which are capable of retaining the wall 24 with spacing from the external wall 22.

The external wall 22 is formed by a tubular armature 28 having a centre axis X-X' which comprises a trellis of interwoven wires 30. The trellis 30 is obtained by braiding at least one wire of stainless steel, a shape-memory alloy or a polymer. In a variant, the trellis 30 is obtained by laser-cutting a tube.

The trellis 30 can be deployed between a contracted state, in which it has a small diameter, and a dilated state, which constitutes the rest state thereof, in which it has a large diameter.

In the example illustrated in FIG. 1, the trellis 30 can be deployed spontaneously between the contracted state and the dilated state thereof.

The armature 28 has an outer surface 32 which is intended to be pressed against the internal wall 12 of the vessel 14 and an inner surface 34 which extends in register with the internal wall 24. The surfaces 32 and 34 extend between a proximal edge 36 which is located at the bottom in FIG. 1, and a distal edge 38 which is located at the top in FIG. 1.

The armature 28 internally defines a central passage 40 having an axis X-X' with a large diameter. The passage 40 opens in the vessel 14 in the region of the proximal edge 36 and the distal edge 38.

In the dilated state thereof, the armature 28 has a diameter greater than 25 mm, for example, of between 25 mm and 60 mm.

The internal peripheral wall 24 is formed by a flexible tube 42 which is produced from fabric. The material used to produce the tube is, for example, Dacron or another woven or knitted polymer.

The flexible tube 42 is arranged completely in the passage 40, in a proximal manner relative to the distal edge 38 and in a distal manner relative to the proximal edge 36. It thus has a length, taken along the axis X-X', which is less than the length of the external peripheral wall 22. The tube 42 internally delimits an aperture 44 which opens in the region of the distal edge 46 and the proximal edge 48 of the tube 42.

The aperture 44 has a substantially constant cross-section having a diameter which is less than 35 mm and, for example, between 15 mm and 35 mm. In this example, the ratio of the mean cross-section of the aperture 44 to the mean cross-section of the central passage 40 is less than 0.9.

The tube 42 has an outer diameter which is less than the inner diameter of the armature 28. The outer surface of the tube 42 is thus positioned completely spaced-apart from the inner surface 34 in the passage 40.

The connection means 26 comprise a proximal connection skirt 52 and a distal connection skirt 54. In the example illustrated in FIG. 1, the skirts 52, 54 are integral with the tube 42 which they extend at the ends thereof.

In this manner, the proximal connection skirt 52 connects the proximal edge 48 of the tube 42 to the proximal edge 36 of the armature 28 and the distal connection skirt 54 connects the distal edge 46 of the tube 42 to the distal edge of the armature 28. The skirts 52, 54 extend in a peripheral manner around the axis X-X' from the edges 46, 48 thereof transversely relative to the axis X-X', respectively.

The distal skirt 54 has a cross-section, taken in an axial centre plane, which diverges towards the distal edge 38 of the armature 28, whilst the proximal skirt 52 has a cross-section which diverges towards the proximal edge 36.

The skirts 52, 54 and the tube 42 delimit, towards the axis X-X' in the central passage 40, an inner region 56 for the flow of blood and, remote from the axis X-X', an annular outer region 58.

The inner region 56 comprises the aperture 44 and opens in the vessel 14 in the region of the edges 36 and 38 of the armature 26. The outer region 58 is delimited, on the one hand, by the outer surfaces of the skirts 54, 52 and the tube 42 and, on the other hand, by the inner surface 34 of the armature 28.

A fluid-tight coating is applied to the material which forms the tube 42 and to the skirts 52, 54 in order to isolate the outer region 58 in a fluid-tight manner with respect to the inner region 56 and to force the blood which flows in the vessel 14 to pass into the inner region 56 through the aperture 44, without passing via the outer region 58.

In this example, the valve 18 is an endovalve which comprises a tubular endoprosthesis 70 and a flexible shutter 72 which is fixed in the endoprosthesis 70. The valve 18 can be moved relative to the support 16 when it is positioned in the support 16 between an initial storage position remote from the support 16 and a position mounted in the tube 42. It has a length, taken along the axis X-X', which is less than the length of the internal peripheral wall 24 and less than the length of the external peripheral wall 22.

The endoprosthesis 70 is formed by a self-expanding tubular trellis having an axis X-X', which can be deployed spontaneously between a radially retracted configuration and a radially dilated configuration. In the dilated configuration thereof, the endoprosthesis 70 is pressed against an inner surface of the tube 42 in the passage 44, as illustrated in FIG. 1, when the valve occupies its position thereof mounted in the tube 42.

The shutter 72 is produced, for example, from a natural valve of a bovine or ovine animal. In a variant, it is produced from a natural or synthetic tissue.

The shutter 72 comprises a tubular base 74 which is extended upwards by three shutter leaflets 76. The base 74 is fixed to an inner surface of the endoprosthesis 70.

The leaflets 76 are integral with the base 70 which they extend in an upward direction. They are distributed around the axis X-X'. The leaflets 76 can be deformed between a blocking configuration in which they substantially block the inner aperture 44 and a release configuration in which they are positioned against the endoprosthesis 70 in order to allow the flow of blood through the aperture 44.

As known per se, the release device (not illustrated) of the support 16 comprises an inner support for positioning the armature 28 and, for retaining the armature in the contracted state thereof, an outer sheath which covers the armature 28 when it is introduced into the vessel 14.

The armature 28 is thus inserted between the support and the sheath in the contracted state thereof. The sheath is moved towards the proximal end relative to the support in order to uncover the armature 28 and to allow the armature 28 to be deployed.

The tool 20 similarly comprises a support 80 for supporting the valve 18, wires 82 for retaining the valve 18 on the support 80 and an external catheter 84 for introducing the valve 18 into the passage 44. Such a tool is described, for example, in the French Application No. 0310298 by the same applicant.

The positioning of the treatment kit 10 according to the invention in the vessel 14 will now be described.

Initially, the surgeon carries out a percutaneous introduction of the valve support 16 which is mounted on the release device thereof until it has passed the outflow of the right ventricle.

During this introduction, the tubular armature 28 of the valve support 16 is kept in the contracted state thereof which facilitates the passage into the blood circulation vessels. In this state, the material tube 42 and the connection skirts 52, 54 are compressed radially around the axis X-X' between the support and the inner surface 34 of the armature 28.

Then, when the support 16 reaches an adequate position opposite the internal wall 12, the surgeon carries out its release in the vessel 14. To this end, he proximally pulls the retention sheath of the support valve 16 in the contracted state thereof to progressively uncover the armature 28 from the distal edge 38 thereof towards the proximal edge 36 thereof.

This movement brings about the radial expansion of the armature 28, and the application of the external surface 32 of this armature 28 against the internal wall 12 of the vessel, over the entire length of the support 16. In this manner, the support 16 is solidly fixed in the vessel 14, with the risk of its movement being minimised, taking into account the significant contact surface-area between the armature 28 and the internal wall 12.

When the armature 28 is deployed into the dilated state thereof, the skirts 52, 54 become tensioned between the edges 36, 38 of the support 16 and the edges 46, 48 of the tube 42. In this manner, the tube 42 moves radially away from the inner surface 34 and is positioned substantially coaxially relative to the axis X-X'. In this dilated state, the inner diameter of the central passage 40 is at a maximum, and is greater than the diameter of the aperture 44.

Then, as illustrated in FIG. 2, the valve 18 is introduced using the release tool 20 thereof into the inner aperture 44 of the tube 42. The outer catheter 84 is moved in a proximal manner relative to the support 80 in order to uncover the tubular endoprosthesis 70 of the valve 18. Then, the retention wires 82 are relaxed and withdrawn and the tubular endoprosthesis 70 is deployed from a configuration retracted against the support 80 to a dilated configuration. In this dilated configuration, it is pressed against the inner surface of the material tube 42, which allows it to be securely fixed.

Since the diameter of the aperture 44 is significantly less than that of the vessel 14, it is possible to use natural bovine valves having a diameter of less than 35 mm in order to produce the shutter 72, even with patients who have a ventricular outflow tract diameter which is far greater than 35 mm.

During operation, blood flows through the inner region 56 when the leaflets of the shutter 72 are pressed against the endoprosthesis 70 under the action of the blood flow in a first direction. In contrast, the leaflets 76 block the flow of blood through the region 56 when the blood flows in a second direction counter to the first direction.

Figure 3:
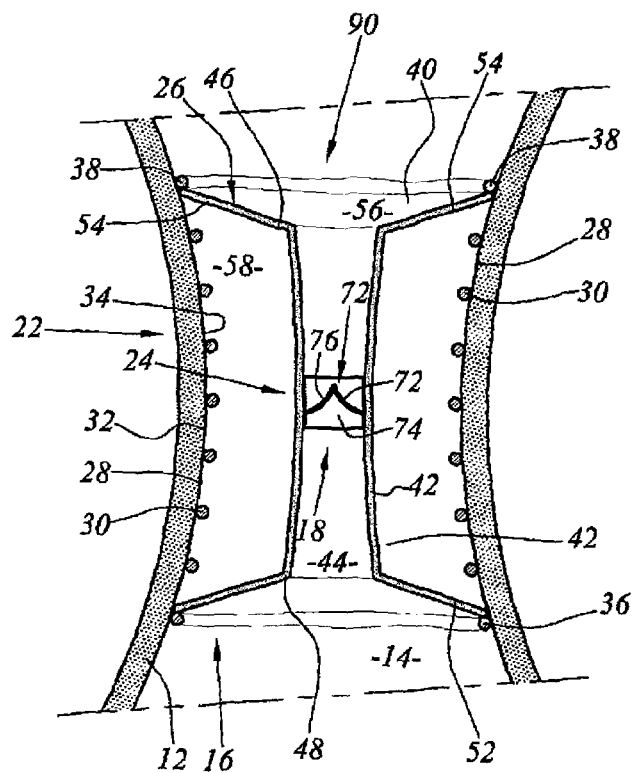
FIG. 3 is a view similar to FIG. 2 of a second treatment kit according to the invention.

The second treatment kit 90 according to the invention, illustrated in FIG. 3, differs from the first kit 10 in that the valve 18 is permanently fixed in the material tube 42 which forms the internal peripheral wall 24. In this manner, the valve support 16 and the valve 18 are introduced simultaneously into the vessel 14 and are moved together in this vessel.

Figure 4:
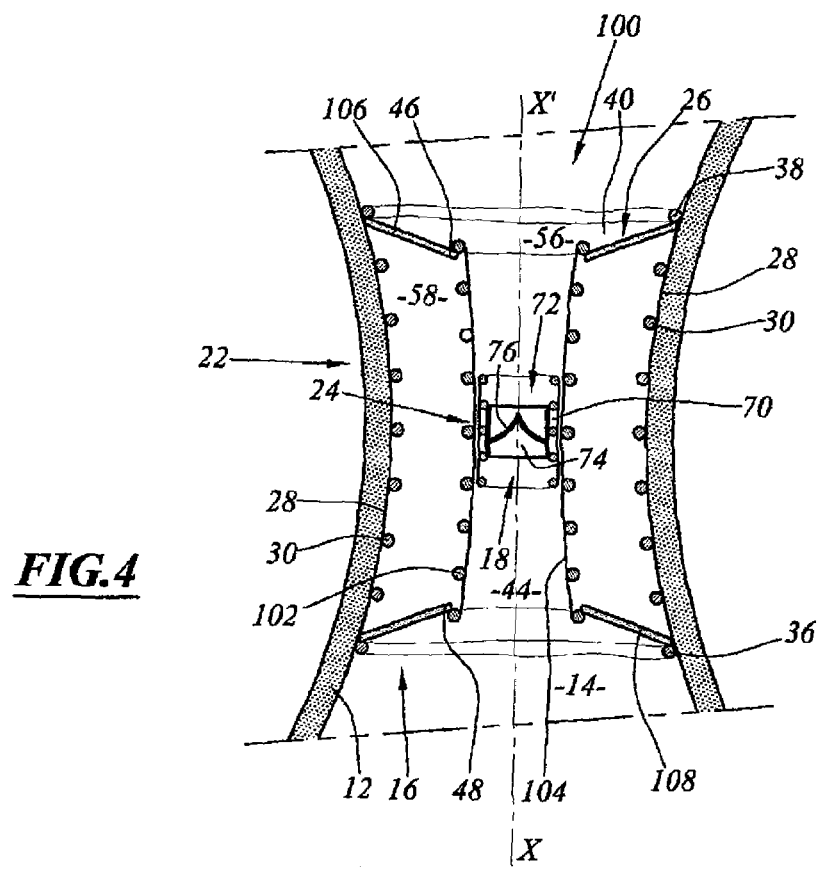
FIG. 4 is a view similar to FIG. 1 of a third treatment kit according to the invention.

A third treatment kit 100 according to the invention is illustrated in FIG. 4. In contrast to the first kit 10, the internal peripheral wall 24 is formed by a self-expanding tubular trellis 102 which is constituted by a plurality of interwoven wires which are embedded in a fluid-tight film of polymer 104.

In this example, the length of the tubular trellis 102, taken along the axis X-X', is substantially equal to the length of the outer armature 28. The connection means 26 are formed by material peripheral collars 106, 108 which connect the distal edges and the proximal edges of the armature 28 and the tubular trellis 102, respectively.

The deployment and the operation of the third kit 100 according to the invention is further similar to that of the first kit.

The fourth kit 120 according to the invention is illustrated in FIGS. 5 and 6. Unlike the first kit 10, the fourth kit 120 is formed by a single tubular armature 122 which is formed by interwoven wires. This armature 122 has a central portion 124 and two end portions 126, 128 which are turned over externally relative to the central portion 124, facing, spaced-apart from and around the central portion.

The central portion 124 forms the internal peripheral wall 24 and delimits the inner aperture 44.

Each end portion 126, 128 comprises an annular peripheral region 130 which extends in register with and remote from the central portion 124, and a bent peripheral region 132 which connects the central portion 124 to the external region 130. Each annular region 130 forms a peripheral wall 22 which is arranged in abutment against the wall 12. Each bent region 132 forms means 26 for connection between the external wall 22 and the internal wall 24.

The proximal end portion 126 and the distal end portion 128 are turned over towards each other, respectively. They each delimit a central passage 40 opening one towards the other. The central portion 124 partially extends in each of the passages 40.

Each end portion 126, 128 can be moved by pivoting the free edge 134 thereof around the bent region 122 between a radially retracted introduction configuration which is partially illustrated in FIG. 6 and a deployed configuration which is illustrated in FIG. 5.

In the introduction configuration, the end portions 126, 128 extend in continuation of the central portion 124, at one side and the other thereof. The support 16 forms a tube having a substantially constant diameter and a maximum length which is illustrated partially in FIG. 6. The distance between the free edges 134 of the portions 126, 128 is at a maximum.

In the deployed operating position thereof, the free edges 134 of each portion 126, 128 have been moved towards each other facing and around the central portion 124. The length of the support 18 is then at a minimum.

Before the support 16 is released in the vessel 14, it is introduced and retained in a catheter 140 in the introduction configuration thereof. Then, the catheter 140 is moved in a proximal manner relative to the armature 122, in order to first bring about the proximal movement of the free edge 134 of the portion 126 which is turned over around the central portion 124. Then, when the armature 122 has been completely uncovered, the free edge 134 of the distal end portion 128 moves towards the free edge 134 of the distal end portion, which causes the proximal end portion 128 to turn up around the central portion 124.

The external regions 130 of the portions 126, 128 are pressed against the inner wall 12 of the vessel 14 in order to retain the support 16 in position. The valve 18 is then introduced into the aperture 44 as described above.

Figure 7:
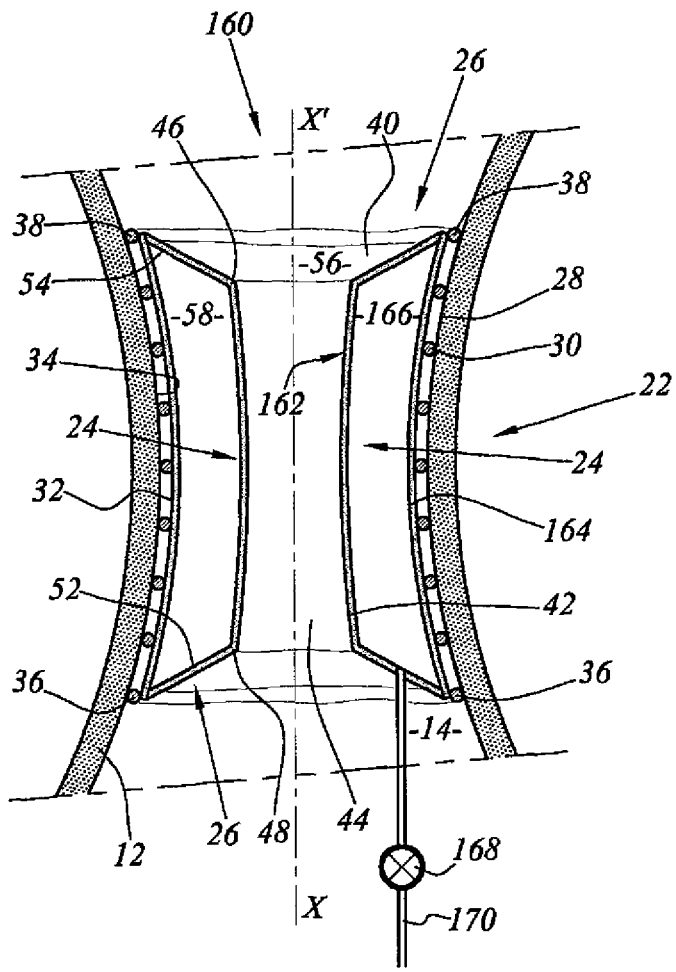
FIG. 7 is a view similar to FIG. 1 of a fifth treatment kit according to the invention, before implantation of a valve in the valve support.

FIG. 7 illustrates a fifth treatment kit 160 according to the invention. Unlike the first kit 10, the valve support comprises an inflatable annular sleeve 162 which is fixed to the inner surface 34 of the armature 28. The sleeve 162 is thus arranged in the central passage 44.

The sleeve 162 comprises a substantially cylindrical inner wall having an axis X-X' which forms the inner peripheral wall 24, and two transverse end walls which form the connection means 26 between the internal wall 24 and the external peripheral wall 22 on the armature 28.

The sleeve 162 is closed externally by a fluid-tight peripheral wall 164 which is fixed to the inner surface 34.

The walls 24, 26 and 164 together delimit a fluid-tight annular space 166 which opens exclusively through a filling valve 168 which protrudes axially in the region of the proximal edge 36 of the armature 28.

The sleeve 162 can be inflated by a liquid being introduced in the space 166 through the valve 168 between a rest configuration, in which the sleeve is deflated and the peripheral wall 24 is pressed against the inner surface, and an inflated configuration, in which the inner peripheral wall 24 extends away from the external peripheral wall 22 in order to delimit an aperture 44 having a cross-section which is smaller than the cross-section of the central passage 40.

When the valve support 16 is introduced into the vessel 14, the sleeve 162 is retained in the rest configuration thereof, which allows the armature 28 to be retained in the contracted state thereof with a minimal diameter.

A catheter 170 for introducing a filling liquid is further connected in a removable manner to the end of the valve 168 during the introduction operation.

After the armature 28 has been deployed and the external peripheral wall 22 has been pressed against the internal surface 12, the valve 168 is opened to introduce liquid into the annular space 166. The sleeve 162 moves into the inflated configuration thereof and the valve 18 can be introduced into the aperture 44, as described above.

After the valve 168 is closed, the catheter 170 is then released from the valve 168 and removed from the vessel 14.

The invention claimed is:

1. A kit for treating a blood circulation vessel, comprising:
a valve support radially deformable between a contracted state and a dilated state, the valve support comprising at least one external peripheral wall which is configured to press against a wall of the blood circulation vessel, the external peripheral wall comprising a tubular armature and having a central passage with a center axis where the external peripheral wall defines a plurality of through openings;
an internal peripheral wall joined to the external peripheral wall, extending along a main axis of the central passage, and delimiting an internal aperture having a radial dimension which is smaller than that of the central passage, the internal peripheral wall extends entirely in the central passage both in the contracted state and the dilated state, the internal peripheral wall comprising a tube made of fabric and arranged completely inside the external peripheral wall, the tube having a total length which is less than a length of the external peripheral wall, wherein the external peripheral wall and the internal peripheral wall define an annular hollow outer region in which the through openings of the external peripheral wall open, and wherein a diameter, length, or width along the main axis of and spanning the through openings is less than the total length of the tube, and wherein the internal peripheral wall and the external peripheral wall are in contact and overlapped with each other when the valve support is in the contracted state;
a first retainer and a second retainer forming a single piece with the tube of the internal peripheral wall, wherein the first retainer and the second retainer retain the internal peripheral wall at least partially with radial spacing from the at least one external peripheral wall, and the first retainer and the second retainer are made of fabric;
a prosthetic valve which comprises a tubular member and a shutter fixed within the tubular member, wherein the prosthetic valve is radially deformable and is configured to be positioned on the internal peripheral wall in the internal aperture in order to selectively block the internal aperture and wherein the tubular member has a length less than the total length of the tube of the internal peripheral wall; and
a layer of fluid-tight material deposited on the first retainer, the second retainer, and the internal peripheral wail to define an inner blood circulation region which opens at proximal and distal ends of the valve support and which contains the internal aperture and an external annular region in order to force blood which flows in the vessel to pass into the inner region through the internal aperture.

2. The kit according to claim 1, wherein the first retainer comprises a distal peripheral skirt and the second retainer comprises a proximal peripheral skirt, wherein the first retainer and the second retainer extend in a space between the internal peripheral wall and the external peripheral wall.

3. The kit according to claim 1, wherein the armature comprises a rigid open-work trellis, and the tube being a flexible tube.

4. The kit according to claim 1, wherein the armature is formed by an external tubular open-work trellis, the tube being formed by an internal open-work trellis which has a diameter smaller than that of the external trellis.

5. The kit according to claim 4, wherein the first retainer comprises a distal peripheral skirt and the second retainer comprises a proximal peripheral skirt, wherein the first retainer and the second retainer extend in the space between the internal peripheral wall and the external peripheral wall.

6. The kit according to claim 1, wherein the valve support comprises an inflatable sleeve which is fixed to the external peripheral wall, the internal peripheral wall being fixed to or delimited by the inflatable sleeve.

7. The kit according to claim 6, wherein the first retainer comprises a distal peripheral skirt and the second retainer comprises a proximal peripheral skirt, wherein the first retainer and the second retainer extend in the space between the internal peripheral wall and the external peripheral wall.

8. The kit according to claim 6, wherein the armature is formed by a rigid open-work trellis, the tube being a flexible tube.

9. The kit according to claim 1, wherein the valve support comprises a single tubular armature which comprises the tube which forms the internal peripheral wall and two end portions of the first and second retainers which are turned over outside and around the tube, each end portion is continuous with the external peripheral wall, and the first retainer and the second retainer retain the internal peripheral wall spaced from the external peripheral wall.

10. The kit according to claim 9, wherein the two end portions are capable of being deformed spontaneously between a configuration for introducing the valve support into the vessel, in which they extend coaxially in continuation of the tube, and an operating configuration, in which they are turned over around the tube.

11. The kit according to claim 1, wherein the internal aperture has a transverse dimension of less than 35 mm.

12. The kit according to claim 1, wherein the tubular member of the prosthetic valve is moveable relative to the internal peripheral wall and comprises a supporting armature.

13. The kit according to claim 1, wherein the prosthetic valve is permanently fixed to the internal peripheral wall.

14. The kit according to claim 1, wherein the tubular armature has an inner surface and the tube has an outer diameter spaced apart from the inner surface of the tubular armature.

15. The kit according to claim 1, wherein the internal peripheral wall extends in the central passage facing the at least one external peripheral wall.

16. The kit according to claim 1, wherein the tubular armature of the at least one external peripheral wall comprises a trellis of interwoven wires with openwork or formed by laser-cutting the tube and the first retainer, where the trellis of interwoven wires define the plurality of through openings of the external peripheral wall, and the first retainer, the second retainer, and the tube of the internal peripheral wall are formed of fabric.

17. A kit for treating a blood circulation vessel, comprising:
   a valve support radially deformable between a contracted state and a dilated state, the valve support comprising at least one external peripheral wall which is configured to press against a wall of the blood circulation vessel, the external peripheral wall comprising a tubular armature and having a central passage with a center axis where the external peripheral wall defines a plurality of through openings;
   an internal peripheral wall fixedly joined to the external peripheral wall, extending along a main axis of the central passage, and delimiting an internal aperture having a radial dimension which is smaller than that of the central passage, the internal peripheral wall comprising a tube made of fabric and arranged completely inside the external peripheral wall, the tube having a total length which is less than a length of the external peripheral wall, wherein the external peripheral wall and the internal peripheral wall define an annular hollow outer region in which the through openings of the external peripheral wall open, and wherein a diameter, length, or width along the main axis of and spanning the through openings is less than the total length of the tube, and wherein the internal peripheral wall and the external peripheral wall are in contact and overlapped with each other when the valve support is in the contracted state;
   a distal peripheral skirt and a proximal peripheral skirt coupled to the tube of the internal peripheral wall, wherein the distal peripheral skirt and the proximal peripheral skirt extend in a space between the internal peripheral wall and the external peripheral wall to retain the internal peripheral wall at least partially with radial spacing from the at least one external peripheral wall;
   a prosthetic valve which comprises a tubular member and a shutter fixed within the tubular member, wherein the prosthetic valve is radially deformable and is configured to be positioned on the internal peripheral wall in the internal aperture in order to selectively block the internal aperture and wherein the tubular member has a length less than the total length of the tube of the internal peripheral wall; and
   a layer of fluid-tight material deposited on the distal peripheral skirt, the proximal peripheral skirt, and the internal peripheral wall to define an inner blood circulation region which opens at proximal and distal ends of the valve support and which contains the internal aperture and an external annular region in order to force blood which flows in the vessel to pass into the inner region through the internal aperture.

18. The kit according to claim 17, wherein the internal peripheral wall extends entirely in the central passage both in the contracted state and the dilated state.

19. The kit according to claim 17, wherein the tubular armature of the at least one external peripheral wall comprises a trellis of interwoven wires with openwork or formed by laser-cutting the tube where the trellis of interwoven wires define the openings of the external peripheral wall, and the distal peripheral skirt, the proximal peripheral skirt, and the tube of the internal peripheral wall are formed of fabric.

* * * * *